US00PP30985P2

(12) United States Plant Patent
van den Haak

(10) Patent No.: US PP30,985 P2
(45) Date of Patent: Oct. 29, 2019

(54) ***ANEMONE* PLANT NAMED 'IFANFB'**

(50) Latin Name: *Anemone hupehensis*
Varietal Denomination: IFANFB

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 15/999,926

(22) Filed: Aug. 31, 2018

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Anemone* plant named 'IFANFB', characterized by its upright and relatively compact plant habit; moderately vigorous to vigorous growth habit; early and freely flowering habit; long flowering period; large semi-double flowers that are red purple in color; and good garden performance.

2 Drawing Sheets

Botanical designation: *Anemone hupehensis.*
Cultivar denomination: 'IFANFB'.

BACKGROUND OF THE INVENTION

The present invention relates to a new and distinct cultivar of *Anemone*, botanically known as *Anemone hupehensis* and hereinafter referred to by the name 'IFANFB'.

The new *Anemone* plant is a product of a planned breeding program conducted by the Inventor in Heerhugowaard, The Netherlands. The objective of the breeding program is to create new compact and vigorous *Anemone* plants with numerous attractive flowers.

The new *Anemone* plant originated from a cross-pollination made by the Inventor in October, 2012 in Heerhugowaard, The Netherlands of a proprietary selection of *Anemone hupehensis* identified as code number 148-10-K001-01, not patented, as the female, or seed, parent with a proprietary selection of *Anemone hupehensis* identified as code number 148-10-K006-01, not patented, as the male, or pollen, parent. The new *Anemone* plant was discovered and selected by the Inventor as a single flowering plant within the progeny of the stated cross-pollination in a controlled greenhouse environment in Heerhugowaard, The Netherlands in October, 2013.

Asexual reproduction of the new *Anemone* by in vitro meristem culture in a controlled environment in Heerhugowaard, The Netherlands since the spring of 2014 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'IFANFB'. These characteristics in combination distinguish 'IFANFB' as a new and distinct *Anemone* plant:

1. Upright and relatively compact plant habit.
2. Moderately vigorous to vigorous growth habit.
3. Early and freely flowering habit.
4. Long flowering period.
5. Large semi-double flowers that are red purple in color.
6. Good garden performance.

Plants of the new *Anemone* can be compared to plants of the female parent selection. Plants of the new *Anemone* differ primarily from plants of the female parent selection in the following characteristics:

1. Plants of the new *Anemone* are more freely flowering than plants of the female parent selection.
2. Flowers of plants of the new *Anemone* are darker red purple in color than flowers of plants of the female parent selection.

Plants of the new *Anemone* can be compared to plants of the male parent selection. Plants of the new *Anemone* differ primarily from plants of the male parent selection in the following characteristics:

1. Flowers of plants of the new *Anemone* have more sepals than flowers of plants of the male parent selection.
2. Flowers of plants of the new *Anemone* are darker red purple in color than flowers of plants of the male parent selection.

Plants of the new *Anemone* can be compared to plants of *Anemone hupehensis* 'Pocahontas', disclosed in U.S. Plant Pat. No. 25,352. In side-by-side comparisons, plants of the new *Anemone* and 'Pocahontas' differ primarily in the following characteristics:

1. Flowers of plants of the new *Anemone* are larger than flowers of plants of 'Pocahontas'.
2. Plants of the new *Anemone* have red purple-colored flowers whereas plants of 'Pocahontas' have light purple-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'IFANFB' in a container.

The photograph at the top of the second sheet comprises a close-up view of typical leaves of 'IFANFB'.

The photograph at the bottom of the second sheet comprises a close-up view of typical flowers and flower buds of 'IFANFB'.

DETAILED BOTANICAL DESCRIPTION

The aforementioned photographs and following observations, measurements and values describe plants grown during the late summer and early autumn in 17-cm containers in an outdoor nursery in Heerhugowaard, The Netherlands and under cultural practices typical of commercial *Anemone* production. During the production of the plants, day temperatures ranged from 15° C. to 25° C. and night temperatures ranged from 8° C. to 20° C. Plants were 21 weeks old when the photographs and description were taken. In the following description, color references are made to The Royal Horticultural Society Colour Chart, 2015 Edition, except where general terms of ordinary dictionary significance are used.

Botanical classification: *Anemone hupehensis* 'IFANFB'.

Parentage:

*Female, or seed, parent*.—Proprietary selection of *Anemone hupehensis* identified as code number 148-10-K001-01, not patented.

*Male, or pollen, parent*.—Proprietary selection of *Anemone hupehensis* identified as code number 148-10-K006-01, not patented.

Propagation:

*Type*.—In vitro meristem culture.

*Time to initiate roots, summer*.—About ten days at temperatures about 22° C.

*Time to initiate roots, winter*.—About 15 days at temperatures about 20° C.

*Time to produce a rooted young plant, summer*.—About 42 days at temperatures about 20° C.

*Time to produce a rooted young plant, winter*.—About 50 days at temperatures about 20° C.

*Root description*.—Fine, fibrous; close to N199C to N199D in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; upright and relatively compact plant habit with leaves developing from basal rosettes; numerous basal rosettes developing per plant; oblong in overall shape; moderately vigorous to vigorous growth habit; moderate growth rate.

*Plant height, soil level to top of foliar plane*.—About 21.4 cm.

*Plant height, soil level to top of floral plane*.—About 46.4 cm.

*Plant diameter*.—About 38.1 cm.

Leaf description:

*Arrangement, basal leaves*.—Alternate; simple.

*Arrangement, cauline leaves*.—Opposite; simple.

*Length, basal leaves*.—About 7.8 cm.

*Width, basal leaves*.—About 7 cm.

*Length, cauline leaves*.—About 6.8 cm.

*Width, cauline leaves*.—About 5 cm.

*Shape, basal leaves*.—Broadly ovate; three-lobed to trifoliate.

*Shape, cauline leaves*.—Ovate to narrowly ovate; three-lobed to trifoliate.

*Apex, basal and cauline leaves*.—Acute.

*Base, basal leaves*.—Hastate.

*Base, cauline leaves*.—Attenuate.

*Margin, basal and cauline leaves*.—Dentate to serrulate tri-lobed, depth of sinuses are medium to very deep and divergent.

*Aspect, basal leaves*.—About 25° from vertical.

*Aspect, cauline leaves*.—About 45° from vertical.

*Texture and luster, basal and cauline leaves, upper surface*.—Sparsely to moderately pubescent; slightly glossy.

*Texture and luster, basal and cauline leaves, lower surface*.—Very sparsely pubescent; matte.

*Venation pattern, basal and cauline leaves*.—Laciniate.

*Color, basal and cauline leaves*.—Developing leaves, upper surface: Close to 143A. Developing leaves, lower surface: Close to 138B. Fully expanded leaves, upper surface: Close to between 147A and N189A; venation, close to 146B to 146C. Fully expanded leaves, lower surface: Close to 147B; venation, close to 144A.

*Leaf petioles*.—Length, basal leaves: About 11.1 cm. Diameter, basal leaves: About 1.75 mm. Length, cauline leaves: About 2.7 cm. Diameter, cauline leaves: About 2.5 mm. Strength, basal and cauline leaves: Strong. Texture and luster, basal and cauline leaves, upper and lower surfaces: Moderately pubescent; glossy. Color, basal and cauline leaves, upper and lower surfaces: Close to 144A.

*Stipules*.—Quantity and arrangement: Two, opposite at the base of each leaf. Length: About 1.9 cm. Diameter: About 3 mm. Shape: Narrowly oblong Texture, upper surface: Smooth, glabrous. Texture, lower surface: Sparsely pubescent. Color, upper and lower surfaces: Close to 144A.

Flower description:

*Flower arrangement and flowering habit*.—Semi-double rotate flowers arranged in simple and compound cymes; freely flowering habit with 550 flowers developing per plant during the flowering season; flowers face mostly upright to slightly outwardly.

*Fragrance*.—None detected.

*Natural flowering season*.—Plants of the new *Anemone* flower during the summer into the late summer in The Netherlands.

*Flower longevity*.—Individual flowers last about seven to ten days on the plant; flowers not persistent.

*Inflorescence height*.—About 28.8 cm.

*Inflorescence diameter*.—About 13.7 cm.

*Flower diameter*.—About 6.1 cm.

*Flower length* (*depth*).—About 2.6 cm.

*Flower buds*.—Length: About 9 mm. Diameter: About 9 mm. Shape: Globular. Texture and luster: Densely pubescent; matte. Color: Close to N186C; proximally, close to 143C.

*Petals*.—Absent.

*Sepals*.—Quantity and arrangement: About 28 arranged in about three whorls. Length: About 2.9 cm to 3.3 cm. Width: About 1 cm to 1.5 cm. Shape: Obovate to oblanceolate. Apex: Obtuse to broadly acute. Base: Cuneate. Margin: Entire. Texture and luster, upper surface: Smooth, glabrous; velvety; matte. Texture and luster, lower surface: Densely pubescent; slightly glossy. Color: When opening, upper surface: Close to 70B; center, close to 69D. When opening, lower surface: Close to 70B to 70C. Fully opened, upper surface: Close to 70B; fading towards the base, close to 75B and N75D; venation, similar to lamina colors; colors do not change with development. Fully opened, lower surface: Close to between 70B and 70C; venation, similar to lamina color; color does not change with development.

*Peduncles*.—Length: About 28 cm. Diameter: About 2 mm. Aspect: About 10° from vertical. Strength: Strong. Texture and luster: Densely pubescent; moderately glossy. Color: Close to 144A.

*Pedicels*.—Length: About 9.9 cm. Diameter: About 1.5 mm. Aspect: About 27.5° from the peduncle axis. Strength: Moderately strong. Texture and luster: Densely pubescent; slightly glossy. Color: Close to 138B.

*Flower bracts*.—Quantity per flower: Two. Length: About 1.7 cm. Width: About 1.2 cm. Shape: Obovate. Apex: Acute. Base: Cuneate. Margin: Entire; distally, serrate. Texture, upper and lower surfaces: Smooth, glabrous. Color, upper surface: Close to 143A to 143B. Color, lower surface: Close to 143A to 143B; margins, close to between N186C and 200A.

*Reproductive organs*.—Androecium: Stamen number per flower: About 160. Filament length: About 4.5 mm. Filament color: Close to between 150D and 155A. Anther shape: Oblong. Anther length: About 1.5 mm. Anther diameter: About 0.5 mm. Anther color: Close to 15A. Amount of pollen: Moderate. Pollen color: Close to 11D. Gynoecium: Pistil number per flower: About 240. Pistil length: About 1 mm. Stigma shape: Club-shaped. Stigma length: About 0.5 mm. Stigma diameter: About 0.5 mm. Stigma color: Close to N144A. Style length: About 0.5 mm. Style color: Close to 150D. Ovary color: Close to 144A.

*Seeds and fruits*.—To date, seed and fruit development have not been observed on plants of the new *Anemone*.

Garden performance: Plants of the new *Anemone* have been observed to have good garden performance, to tolerate high temperatures of about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'IFANFB' as illustrated and described.

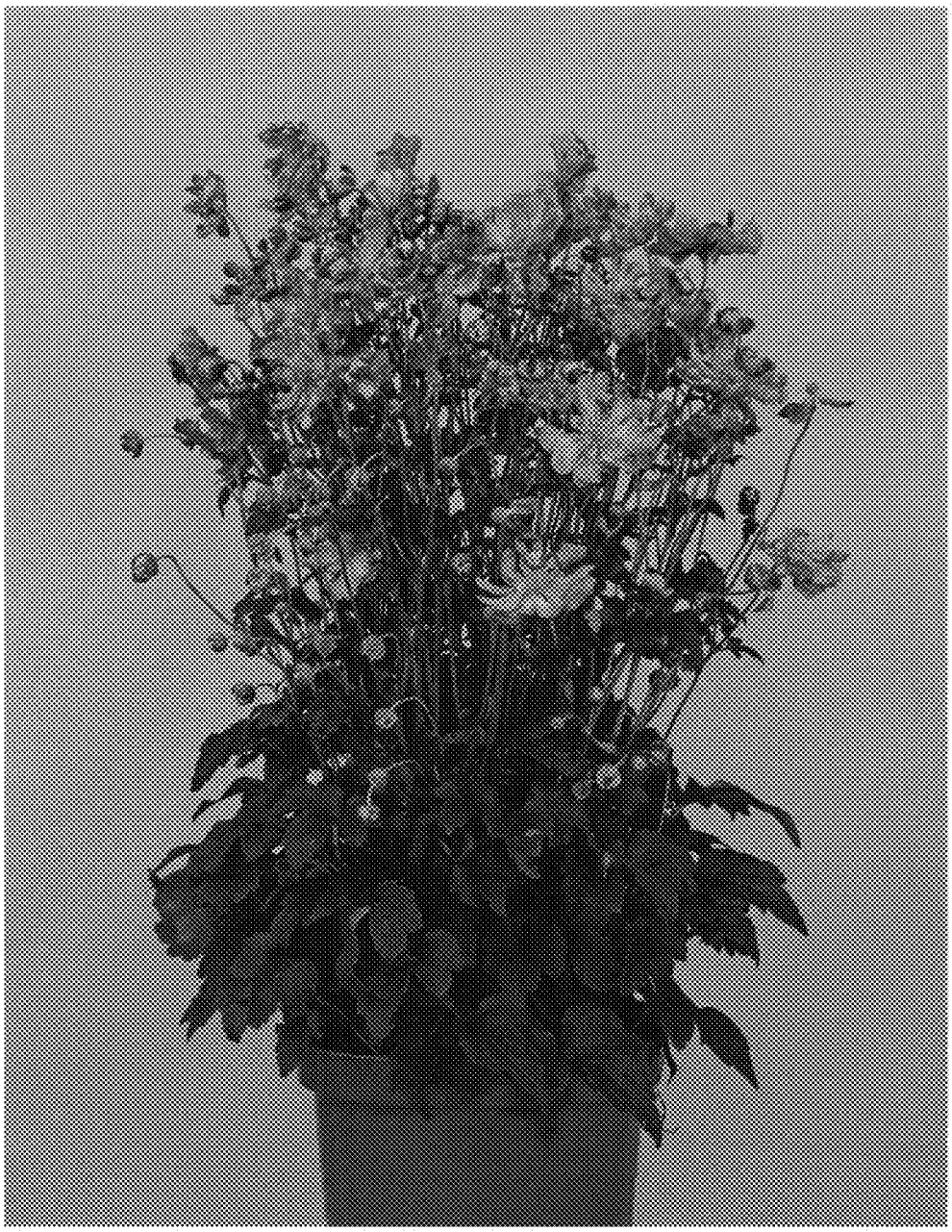

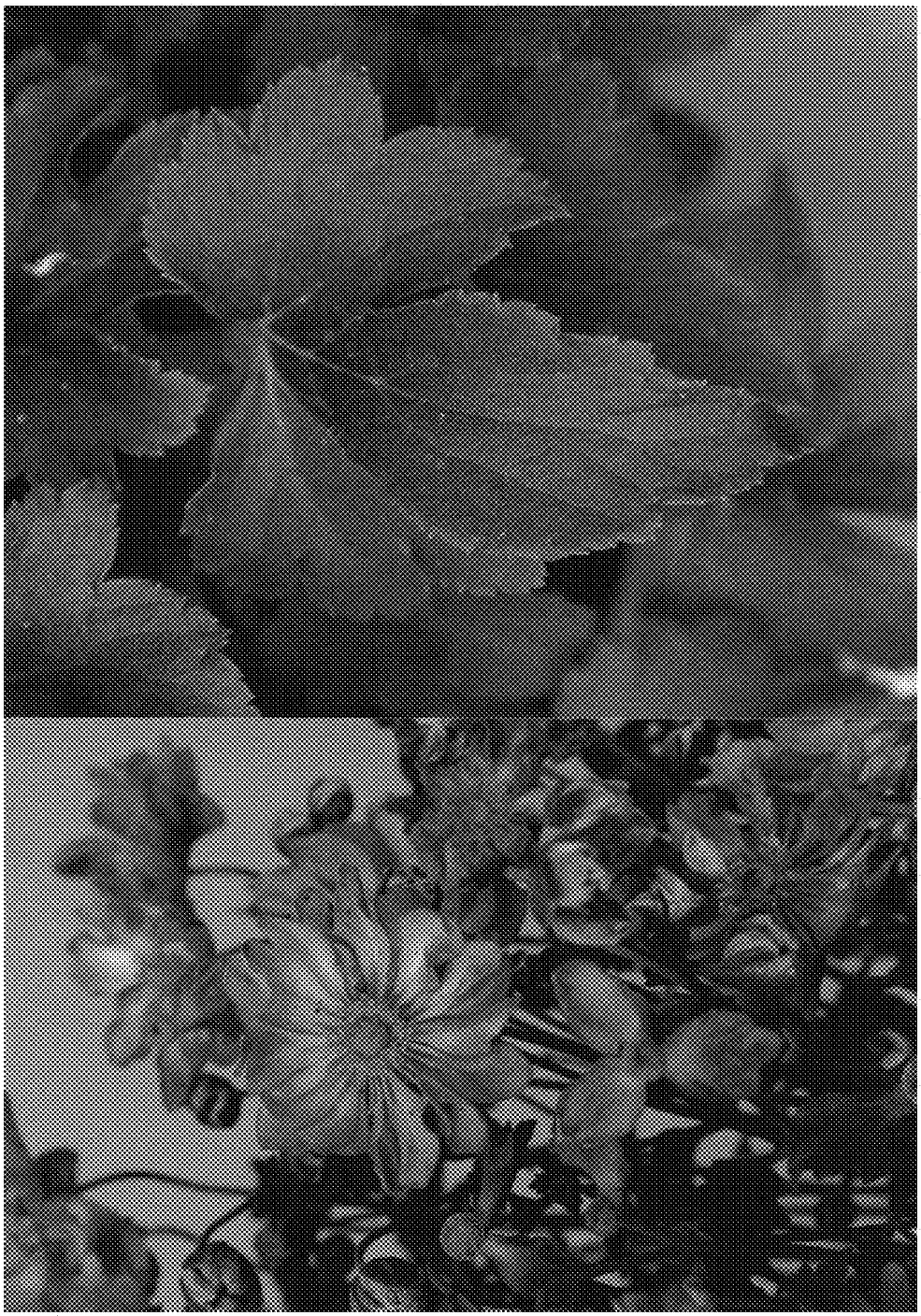

* * * * *